US010827968B2

(12) United States Patent
Kwatra et al.

(10) Patent No.: US 10,827,968 B2
(45) Date of Patent: Nov. 10, 2020

(54) EVENT DETECTION AND NOTIFICATION SYSTEM

(71) Applicant: International Business Machines Corporation, Armonk, NY (US)

(72) Inventors: Shikhar Kwatra, Durham, NC (US); John D. Wilson, League City, TX (US); Jeremy R. Fox, Georgetown, TX (US); Corville O. Allen, Morrisville, NC (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/372,483

(22) Filed: Apr. 2, 2019

(65) Prior Publication Data
US 2020/0315515 A1 Oct. 8, 2020

(51) Int. Cl.
*A61B 5/00* (2006.01)
*G08B 21/04* (2006.01)

(52) U.S. Cl.
CPC .......... *A61B 5/4064* (2013.01); *G08B 21/043* (2013.01); *G08B 21/0446* (2013.01); *G08B 21/0476* (2013.01)

(58) Field of Classification Search
CPC . G01L 5/0052; H04L 9/3231; H04L 63/0861; G07C 9/37; H04W 12/06;
(Continued)

(56) References Cited
U.S. PATENT DOCUMENTS 8,223,024 B1 * 7/2012 Petrou ..................... G06F 3/011
340/573.1
8,812,344 B1 * 8/2014 Saurabh ............. G06Q 30/0201
705/7.29
(Continued)

FOREIGN PATENT DOCUMENTS

EP 3346402 A1 11/2018

OTHER PUBLICATIONS

Chen et al., "An Accurate Crowdsourcing-Based Adaptive Fall Detection Approach Using Smart Devices," 2016 IEEE International Conference on Healthcare Informatics (ICHI), Chicago, IL, © 2016, pp. 456-460.
(Continued)

*Primary Examiner* — Hoi C Lau
(74) *Attorney, Agent, or Firm* — William H. Hartwell; Issac J. Gooshaw

(57) ABSTRACT

Embodiments of the present invention provide a method, system, and program product for event detection and/or notification of events occurring. A user monitoring system sends messages based on determinations of impacts associated with the user. The monitoring system receives data from at least one computing device affixed to a user. The data corresponds to a pattern of movement of the user. The monitoring system determines that the user is performing an activity that has an associated known pattern of impacts. The system generates a customized pattern of impacts for the activity by modifying the known pattern of impacts based on the pattern of movement of the user. The system generates a message based on a comparison of measured movement data of the user and the customized pattern of impacts.

20 Claims, 6 Drawing Sheets

(58) Field of Classification Search
CPC ............ G08B 25/001; G06K 9/00711; G06K 9/00342; G06K 9/0053; A61B 5/11; A61B 5/7405
See application file for complete search history.

(56) References Cited

U.S. PATENT DOCUMENTS

| | | | |
|---|---|---|---|
| 8,925,118 B2 | 1/2015 | Pietrantonio | |
| 10,232,861 B2* | 3/2019 | Huang | B60W 50/14 |
| 10,520,378 B1* | 12/2019 | Brown | A61B 5/11 |
| 2005/0063595 A1* | 3/2005 | Bissonnette | A63B 69/3658 382/218 |
| 2008/0281638 A1 | 11/2008 | Weatherly et al. | |
| 2009/0048540 A1* | 2/2009 | Otto | A61B 5/1117 600/595 |
| 2011/0144539 A1 | 6/2011 | Ouchi | |
| 2011/0270135 A1* | 11/2011 | Dooley | G16H 50/30 600/595 |
| 2012/0088544 A1* | 4/2012 | Bentley | A63F 13/92 455/556.1 |
| 2013/0128022 A1* | 5/2013 | Bose | G06K 9/00342 348/77 |
| 2013/0303946 A1 | 11/2013 | Gettens | |
| 2014/0085050 A1* | 3/2014 | Luna | G07C 9/37 340/5.82 |
| 2014/0089672 A1* | 3/2014 | Luna | H04L 9/3231 713/186 |
| 2014/0089673 A1* | 3/2014 | Luna | H04L 63/0861 713/186 |
| 2014/0266791 A1* | 9/2014 | Lloyd | G08B 21/0423 340/870.09 |
| 2016/0292881 A1* | 10/2016 | Bose | G06K 9/00711 |
| 2016/0296153 A1 | 10/2016 | Lovoi | |
| 2016/0307335 A1* | 10/2016 | Perry | H04N 5/23229 |
| 2016/0322078 A1* | 11/2016 | Bose | A63F 13/217 |
| 2016/0335398 A1 | 11/2016 | Kozloski et al. | |
| 2016/0369504 A1 | 12/2016 | Kim et al. | |
| 2017/0004358 A1* | 1/2017 | Bose | G06K 9/0053 |
| 2017/0061817 A1* | 3/2017 | Mettler May | G09B 19/003 |
| 2017/0071526 A1 | 3/2017 | Lyren | |
| 2017/0124699 A1 | 5/2017 | Lane | |
| 2017/0189752 A1* | 7/2017 | Mohrman | G01C 21/16 |
| 2017/0200359 A1* | 7/2017 | Gregg | G08B 25/001 |
| 2017/0262697 A1* | 9/2017 | Kaps | G11B 27/022 |
| 2017/0272842 A1* | 9/2017 | Touma | H04Q 9/00 |
| 2017/0368413 A1* | 12/2017 | Shavit | G06K 9/00342 |
| 2018/0043906 A1* | 2/2018 | Huang | B60W 50/14 |
| 2018/0244279 A1* | 8/2018 | Kochhar | G08B 21/06 |
| 2018/0264320 A1* | 9/2018 | Chang | A63B 24/0062 |

OTHER PUBLICATIONS

Cippitelli et al. "An Integrated Approach to Fall Detection and Fall Risk Estimation Based on RGB-Depth and Inertial Sensors," In Proceedings of the 7th International Conference on Software Development and Technologies for Enhancing Accessibility and Fighting Info-exclusion (DSAI 2016), ACM, New York, NY, USA, pp. 246-253.

Saunier et al., "Large-Scale Automated Analysis of Vehicle Interactions and Collisions," Transportation Research Record: Journal of the Transportation Research Board, vol. 2147, Published 2010, 20 pages.

Wallace et al.,"Exploring clinical correlations in centroid-based gait metrics from depth data collected in the home," In Proceedings of the 11th EAI International Conference on Pervasive Computing Technologies for Healthcare (PervasiveHealth '17). May 23-26, 2017, ACM, Barcelona, Spain, pp. 203-206.

* cited by examiner

US 10,827,968 B2

EVENT DETECTION AND NOTIFICATION SYSTEM

BACKGROUND OF THE INVENTION

The present invention relates generally to the field of impact notification, and more particularly to a system that warns of detected and/or predicted impacts.

Smart devices and information appliances are becoming increasingly prevalent in many societies around the world. in general, such devices include or have access to sensor data regarding a specific environment. Such devices are becoming more mobile and can now be found in many forms of wearable or otherwise portable devices that can be carried or worn by a user throughout their daily activities. Several notable types of smart devices include, but are not limited to, smartphones, phablets and tablets, smartwatches, smart bands, smart key chains, and smart headphones.

SUMMARY

Embodiments of the present invention provide a method, system, and program product for event detection and/or notification of events occurring.

One aspect of the invention provides a computer implemented method. The method comprising: receiving, by one or more computer processors, data from at least one computing device affixed to the user, wherein the data corresponds to a pattern of movement of a user; determining, by the one or more computer processors, that a user is performing an activity that has an associated known pattern of impacts; generating, by the one or more computer processors, a customized pattern of impacts for the activity by modifying the known pattern of impacts based, at least in part, on the pattern of movement of the user; and generating, by the one or more computer processors, a message based at least in part, on a comparison of measured movement data of the user and the customized pattern of impacts.

Another aspect of the invention provides a computer program product embodied as program instructions stored on a computer readable storage medium. The program instructions comprising instructions to cause a computing device to perform a method, the method comprising: receiving data from at least one computing device affixed to a user, wherein the data corresponds to a pattern of movement of the user; determining that the user is performing an activity that has an associated known pattern of impacts; generating a customized pattern of impacts for the activity by modifying the known pattern of impacts based, at least in part, on the pattern of movement of the user; and generating a message based, at least in part, on a comparison of measured movement data of the user and the customized pattern of impacts.

Another aspect of the invention provides a computer system. The computer system including program instructions stored on a computer readable storage medium that, when executed by the computer system, causes the computer system to perform a method, the method comprising: receiving data from at least one computing device affixed to a user, wherein the data corresponds to a pattern of movement of the user; determining that the user is performing an activity that has an associated known pattern of impacts; generating a customized pattern of impacts for the activity by modifying the known pattern of impacts based, at least in part, on the pattern of movement of the user; and generating a message based, at least in part, on a comparison of measured movement data of the user and the customized pattern of impacts.

Still yet, any of the components of the present invention could be deployed, managed, serviced, etc., by a service provider who offers to implement event detection and/or event notification in a computer system. Embodiments of the present invention also provide and encompass related systems, methods, and/or program products.

BRIEF DESCRIPTION OF THE SEVERAL VIEWS OF THE DRAWINGS

These and other features of this invention will be more readily understood from the following detailed description of the various aspects of the invention taken in conjunction with the accompanying drawings.

DETAILED DESCRIPTION

Figure 1:
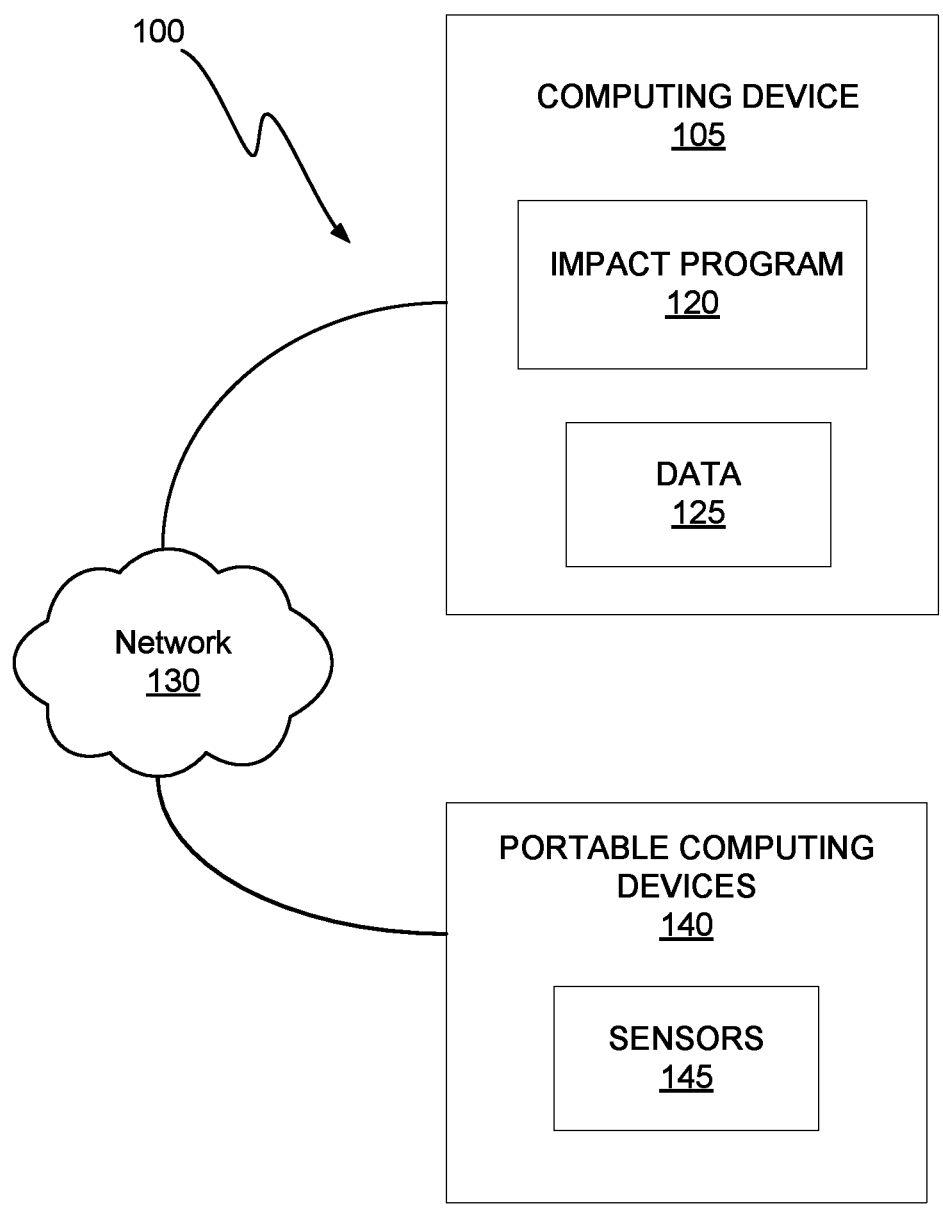
FIG. 1 is a functional block diagram illustrating a computing environment, in accordance with an exemplary embodiment of the present invention.

Penetrating trauma is a type of physical trauma in which an object pierces the skin or body, usually creating an open wound. In contrast, blunt trauma is a type of physical trauma that results from an individual experiencing an impact. Often, blunt trauma is an initial impact trauma from which a person develops more specific types of injury, such as contusions, abrasions, lacerations, and/or bone fractures. Often, physical trauma is the result of unforeseen circumstances or events, such an accidental fall. Some studies have shown that there is a correlation between various factors, such as changes in weather, and the incidence of physical trauma. While some types of physical trauma result in little to no harm to the individual, other more severe instances of physical trauma require medical attention. Further, as the number of physical trauma incidents increase, so do the number of cases of physical trauma that require medical attention. As described herein, embodiments of the present invention identify events that may indicate that a physical trauma has occurred.

Smart devices are becoming increasingly prevalent in many societies around the world. A smart device is an electronic device, generally connected to other devices or networks via different wireless protocols that can operate, to some extent, interactively and autonomously. In general, smart devices include sensors themselves or otherwise have access to sensor data regarding the environment of the smart device. Several notable types of smart devices are smartphones, smart cars, smart thermostats, smart doorbells, smart locks, smart refrigerators, phablets and tablets, smartwatches, smart bands, smart key chains, smart speakers and others. In some instances, the term can also refer to a device that exhibits some properties of ubiquitous computing, including, but is not limited to, artificial intelligence.

Detailed embodiments of the present invention are disclosed herein with reference to the accompanying drawings. In the drawings, like numbering represents like elements. It is to be understood that the disclosed embodiments are merely illustrative of potential embodiments of the present invention and may take various forms. In addition, each of the examples given in connection with the various embodiments is intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

While certain solutions to accident and/or impact are known, these solutions often rely on specialized equipment that is not typically worn by individuals as they go about daily activities. For example, certain specialized sports and occupation equipment includes sensors and other types of data gather devices that can be used to determine whether there is a risk associated with an accident and/or impact. However, this type of equipment is neither prevalent nor is it typically available to the general public. As such, the applicability of such solutions can be seen as limited to only those individuals that wear the specialized equipment, and even then, the applicability is limited to only the times during which the individual is actually wearing the specialized equipment, such as during work hours.

Embodiments of the present invention leverage the prevalence of portable computing devices, which already include certain types of motion sensors and global positioning systems (GPS), to provide an alert system that can warn of impact and potential dangers associated with such impacts.

The present invention will now be described in detail with reference to the Figures.

FIG. 1 is a functional block diagram illustrating a computing environment, generally designated 100, in accordance with one embodiment of the present invention. Computing environment 100 includes computing device 105 and portable computing devices 140 connected over network 130. Computing device 105 includes impact program 120 and data 125. Portable computing devices 140 include sensors 145.

In various embodiments of the present invention, portable computing devices 140 represents one or more computing devices that are either worn or are otherwise being carried with a user. In various embodiments of the present invention, portable computing devices 140 is a computing device that can be a standalone device such, but not limited to, as a smart phone or a smart wristwatch. In general, portable computing devices 140 can be any computing device or a combination of devices that include sensors 145 and travels with and/or is typically worn by users during their daily activities, which includes at least some non-vocation activities. As such, it is to be understood that portable computing devices 140 can be portable computing devices that are available to the general public. Portable computing devices 140 may further include certain internal and external hardware components, as depicted and described in further detail with respect to FIG. 6.

In various embodiments of the present invention, computing device 105 is a computing device that can be a standalone device, a server, a laptop computer, a tablet computer, a netbook computer, a personal computer (PC), or a desktop computer. In another embodiment, computing device 105 and portable computing devices 140 represents a computing system utilizing clustered computers and components to act as a single pool of seamless resources. In general, computing device 105 can be any computing device or a combination of devices with access to program 120 and data 125 and is capable of executing program 120. Computing device 105 may include internal and external hardware components, as depicted and described in further detail with respect to FIG. 6.

Certain embodiments of the present invention, combine the features and functions of computing device 105, as described herein, into those of portable computing devices 140 such that portable computing devices 140 represent any computing device or a combination of devices with access to program 120 and data 125 and is capable of executing program 120.

In this exemplary embodiment, program 120 and data 125 are stored on computing device 105. However, in other embodiments, program 120 and data 125 may be stored externally and accessed through a communication network, such as network 130. Network 130 can be, for example, a local area network (LAN), a wide area network (WAN) such as the Internet, or a combination of the two, and may include wired, wireless, fiber optic or any other connection known in the art. In general, network 130 can be any combination of connections and protocols that will support communications between computing device 105 and computing devices 140, in accordance with a desired embodiment of the present invention.

Figure 2:
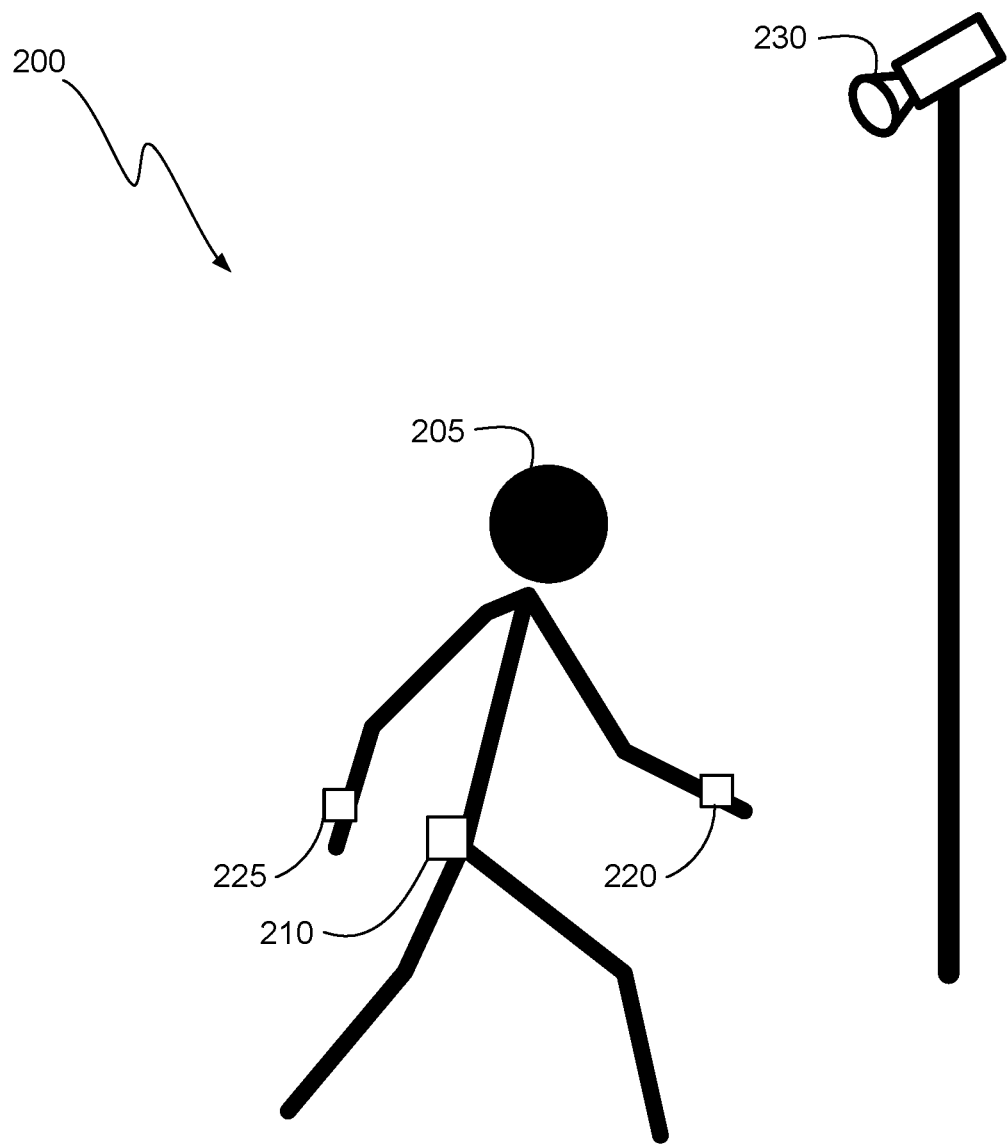
FIG. 2 illustrates a data gathering, in accordance with an exemplary embodiment of the present invention.

FIG. 2 illustrates an example of a data gathering environment, generally designated 200, in accordance with one embodiment of the present invention. As shown in this illustration, a user, 205, includes three portable computing devices 140, herein denoted as smartphone 210 and smart wristwatch 220 and a smart band 225. Also shown is a data source that is external to, i.e., not being worn or carried by, user 205, such as video device 230, that can be leveraged to provide additional details where it is determined that an impact has occurred. Note that such additional sources of data are not limited to stationary video cameras. Some embodiments of the present invention may gather additional data from a variety of data sources that are predicted to have been within the vicinity of user 205 within a time frame associated with the impact, which may include times before, during, or after the impact. This may include, but is not limited to, both stationary devices such as, video device 230, and other portable computing devices that are being worn or are carried by other individuals that are nearby to user 205, i.e., are within a threshold distance. In some embodiments and scenarios, data retrieved from devices like video device 230 is be analyzed by impact program 120 to determine a state of a user and/or an environment of the user. For example, impact program 120 determines that user 205 has experienced an impact that exceeds a threshold. Impact program 120 further determines that user 205 has failed to respond to a query sent by impact program 120. Impact program 120 determines that user 205 is located within a range of video device 230 based on a GPS signal of smartphone 210 of user 205. As such, impact program 120 accesses the video data being generated by video device 230 and performs an image analysis. In this example, the image analysis indicates that user 205 is laying on the ground and impact program 120 determines that user 205 may be unconscious or otherwise unable to respond. In response to this fact pattern, impact program 120 sends an alert message to the nearest first responder since user 205 has likely suffered a serious injury. One having ordinary skill in the art recognizes that, in certain embodiments and scenarios, more or fewer smart devices may be worn by a user, and that further devices may be accessed by the system, and still fall within the scope of the present invention as described herein.

In one embodiment, data 125 includes a repository of movement data that is crowd-sourced and correlates to patterns associated with certain activities. In one embodiment and in one scenario, a user is wearing a smart device on each wrist and has another smart device on them. In such embodiments, impact program 120 analyses the motion of both hands, via movement data supplied by sensors 145 of portable computing devices 140, to determine a likely activity being carried out by user 205. In one such embodiment, the movement data of the user is compared to the known movement patterns included in data 125 and an activity of the user is determined based, at least in part, on matching of the movement data to a known pattern of movement. In some embodiments, likely activities are identified based, at least in part, on historical records, also included in data 125, that indicate the user has previously engaged in a given activity.

For example, a user is at home at 6 PM and is cutting up food for dinner. In a first time period, based, at least in part, on previously identified patterns of movement and on an analysis of the current data from portable computing devices 140, impact program 120 determines that the user is likely using a knife to prepare food, which has an associated known pattern of movement. In one such example, a current activity the user is determined based on a pattern of user movement matching the known pattern to within a threshold. In a subsequent time period, impact program 120 determines that the movement data from portable computing devices 140 has deviated from the pattern of movement associated with using the knife to prepare food. A further analysis of the movement data from portable computing devices 140 matched the deviating portion of data to at least a part of a pattern of movement that is associated with a user accidentally cutting their hand with the knife.

Embodiments recognize that certain patterns of movement may indicate a likely injury of the user. In the above example, a type of injury associated with the use of knife is associated with a pattern of movement that indicates the non-cutting hand, i.e., the hand that is not holding the knife being jerked away from the hand with the knife. Such a signal is different than the normal vectors associated with the use of the knife. As such, impact program 120 learns the nominal behavior of the user as they use the knife, which is based in part on historical data associated with using knifes to prepare food, and then looks for deviations from those patterns that indicate that a possible accident has occurred.

In this example, impact program 120 determined that a penetrating trauma may have occurred along with a potential laceration of the hand of the user.

In response, impact program 120 sends a message to the user with an inquiry regarding the status of the user. In some embodiments, the inquiry is an audio-based message that asks for an update regarding the possible injury of the user. Embodiments of the present invention recognize that certain activities and/or types of injury may dictate the type of message to be sent. Embodiments of the present invention recognize that certain activities and/or potential injuries utilize the hands and that a verbal inquiry may be more likely to solicit a response from the user. In this example, the user was using their hands to prepare food, and in addition, the type of injury may have affected the ability of the user to respond to, for example, a text based query sent to a smart-phone of the user. In this example, impact program 120 determines that the user has a smart-phone on them and that the smart-phone has the needed devices (e.g., a speaker and a microphone) to enable verbal communication with the user. As such, impact program 120 determines that a verbal query is to be used and verbally communicates with the user via the smart-phone. Embodiments recognize that voice recognition techniques are well understood by one having ordinary skill in the art and that such techniques are incorporated with at least some embodiments described herein.

In another example, a person is in their house and hits their thumb with a hammer while hanging a picture on the wall. Impact program 120 is able to differentiate between different types of impact with different tools as well as a likely type of injury. In this example, impact program 120 determined that the user has struck something with the hammer based on impact data associated with the hand that is holding the hammer. However, impact program 120 also determines that within a time period subsequent to the impact, the user exhibited a motion that matched a vigorous shaking of the hand that was holding the nail being hammered. Impact program 120 therefore determines that it is likely that the user struck their hand with the hammer and have sustained a blunt trauma.

As such, while this example and the previous example both include impact based injuries, impact program 120 is able to differentiate between both activities and is able to respond to the different injuries based on the type of injury that matches the pattern of movement. In some instances, impact program 120 accessed a medical database to provide care instructions for the user to treat the injury until further medical attention can be provided. For example, a traumatic head injury may include bleeding from a laceration. As such, impact program 120 instructs the user to provide the appropriate amount of pressure to the wound to slow the bleeding until emergency medical treatment is provided.

Embodiments of the present invention recognize and provide a smart device system that has a data collection application running. In one embodiment, the data collection application is installed on one or more smart devices, e.g., impact program 120 is installed on portable computing devices 140. In other embodiments, the collection application is installed on another computing device that has access to data generated by smart devices. For example, impact program 120 is installed on computing device 105 and has access to data generated by sensors 145 of portable computing devices 140.

Embodiments recognize that assorted smart devices and sensors can connect to applications executing on other smart devices using a variety of wireless communication schemes. For example, a smart watch connects to an application executing on a smart phone application using a near field communication scheme and transmits data to another computing device via the smart phone. In various embodiments, data collected from smart-devices includes impact data in the form of vectors. In some embodiment, the magnitude of the vectors is analyzed to determine what normal, i.e., expected, day to day force exposures, i.e., impacts, are predicted for a given user. In other words, impact program 120 determines what forces a given use is likely to experience during their normal day to day activities. For example, the forces, i.e., impacts, that a user is likely to experience while driving a car, jogging, walking up stairs, and folding laundry etc. In various embodiments, impact program 120 monitors for impacts that deviate from the expected impact patterns. Impact program 120 analyzes impact patterns that deviate from the expected impact pattern to determine whether various criteria have been met that dictate a response from impact program 120. For example, the impact pattern for a user jogging deviates suddenly and impact program 120 determines that subsequent data from the portable computing devices 140 indicate a large impact that correlates to an impact pattern of a user tripping while jogging and falling to the ground. Impact program 120, determines that criteria have been met that dictate the user be contacted and then responds accordingly, e.g., by sending a query to the user and/or contacting emergency medical personnel.

In addition, embodiments recognize that data from a crowd-sourcing level can be collected and leveraged that would show what expected force exposures would be for different collections of people. For example, the jarring forces experienced by people who walk heel first, such that the heel strikes the ground before the toe, is different than the forces experienced by people who walk on the front of their feet, such that their toes impact the ground before their heels. In some instances, such data may have a gaussian distribution with most of the force vectors clustered around a mean and more extreme events being distributed towards the tails of the curve. Various embodiments of impact program 120 leverage such data when determining the forces that a given user is predicted to experience.

Figure 3:
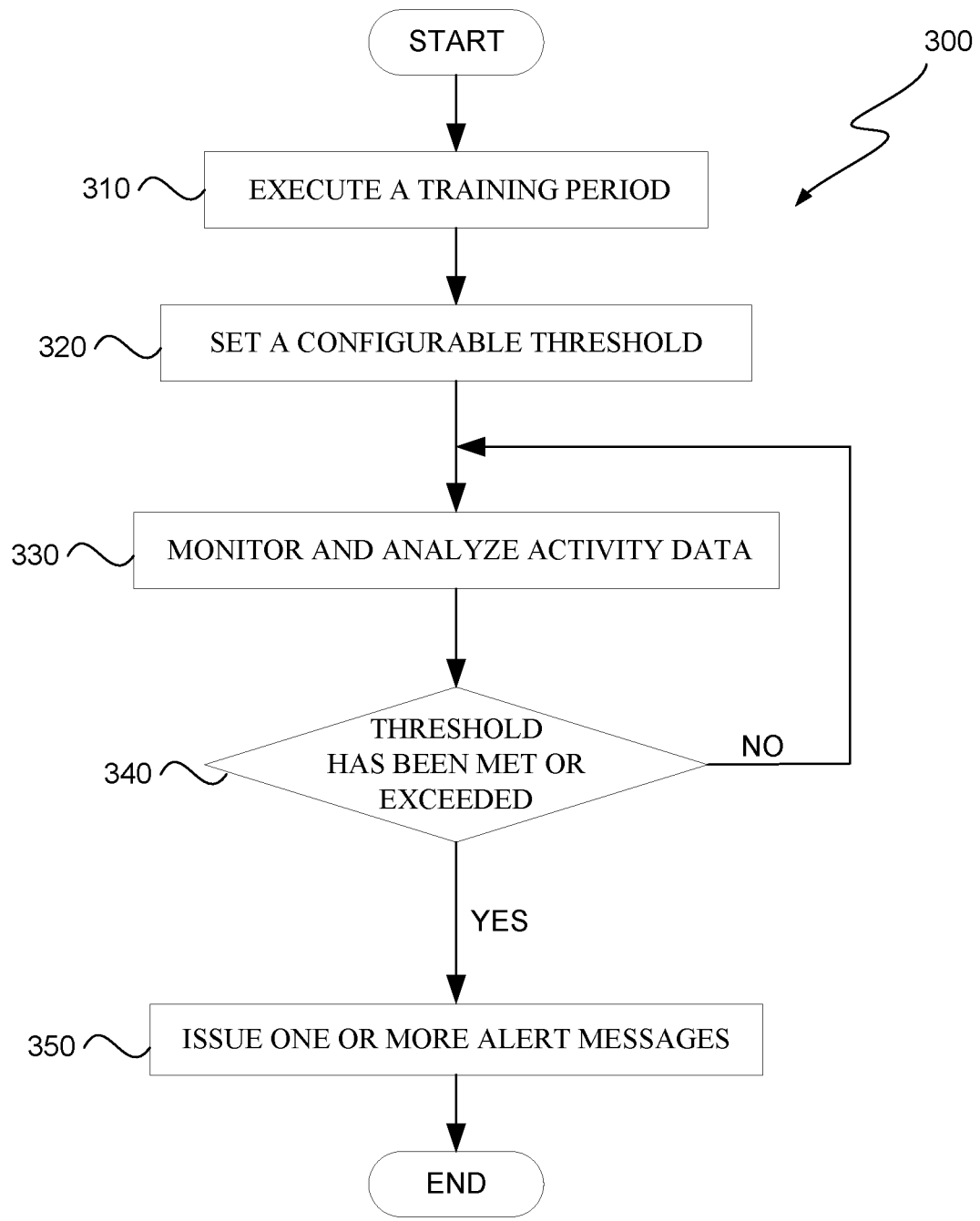
FIG. 3 illustrates a flowchart of operational processes of an impact program, executing on a computing device within the environment of FIG. 1, in accordance with an exemplary embodiment of the present invention.

FIG. 3 illustrates a flowchart, 300, of operational processes of impact program 120, executing on a computing device within the environment of FIG. 1, in accordance with an exemplary embodiment of the present invention.

In process 310, impact program 120 executes a training period during which data, including but is not limited to accelerometer data, is collected. In embodiments, at least a portion of the training data is collected from smart-devices. In general, impact program 120 learns what movements and associated forces are expected to be experienced by a given user. Embodiments recognize that a given type of movement/activity can be identified based on a pattern of forces that a user typically experiences while performing that movement. In some embodiments and scenarios, impact program 120 generates a modified pattern of movement/force/activity for the specific user by modifying a crowd-sourced pattern of movement/force/activity. This modified pattern is then used to determine whether the user is performing that given activity.

For example, impact program 120 determines that the accelerometer data, generated by portable computing devices 140, matches, to within a threshold, a crowd-sourced impact pattern that is associated with jogging, which is included in data 125. Impact program 120 queries user 205 regarding their current activity and receives a confirmation that user 205 is jogging. Impact program 120 generates an impact pattern that is associated with user 205 performing the activity of jogging by modifying the crowd-sourced impact pattern of jogging based on the differences between the crowd-soured impact pattern of jogging and measured accelerometer data that was generated via the movements of the user. As such, impact program 120 generates customized patterns of movement that are correlated to the expected movements of a given user when that user performs the given activity associated with that pattern of movement.

In some embodiments, other training data is retrieved and leveraged that includes one or both of crowd-sourced data and data pertaining to a specific user associated with portable computing devices 140. For example, impact program 120 retrieves crowd-sourced data and data regarding user 205 that indicates that they typically eat their evening meals at around 6 PM each evening. Based, at least in part, on the crowd-sourced data, impact program 120 determines that user 205 is likely to spend 20 to 45 minutes preparing their evening meal each day. As such, impact program 120 monitors data generated by portable computing devices 140 and applies filters to assist in identification of patterns of movement that are associated with various cooking activities that user 205 may perform during a time period preceding 6 PM. In one example, impact program 120 further leverages knowledge of a schedule of user 205, accessible via network 130, to determine that at least some of the movement data generated by portable computing devices 140 between 4 PM and 6 PM is predicted to represent cooking activities. Impact program 120 thus analyzes such impact data using patterns of movement that are specifically associated with food preparation. As such, the ability of impact program 120 to accurately learn patterns of movement that are associated with given activities, and thus to identify actual activities being performed by a user, is increased. This improvement may provide a technological advancement in at least the fields of user activity monitoring and/or proper identification of an activity being performed by a given user.

In process 320, impact program 120 sets a configurable threshold based, at least in part, on the training period for the person being monitored. In general, this threshold dictates the acceptable amount of deviation from a given pattern of impact. If the deviation exceeds the threshold, then impact program 120 determines that an event has occurred that requires further action, such as, for example, sending queries and/or alerting a caregiver. In one embodiment, the threshold is further configured based on feedback from a given user. For example, the threshold is configured based feedback from a caregiver regarding a person being monitored. In another example, an athlete indicates that the threshold be configured based on 2 standard deviations from the mean. In another example, for an individual doing the same thing every day, the threshold is configured based on 1.5 standard deviations from the mean.

In process 330, impact program 120 monitors and analyzes activity data being generated while an activity is being performed by a given user. In some embodiments, the monitoring and analysis takes into account not only measured impacts but also the location and movements of the user. For example, based on the velocity of a user and the impact pattern being generated, impact program 120 determines that the user is skateboarding down a sidewalk. Impact program 120 accesses global positioning (GPS) data of a smart device being worn by the user and determines that the direction of the user. Impact program 120 then combines this information with a map of the area to identify obstacles or structures that pose a higher risk of injury to the user. In this example, impact program 120 determines that a portion of the sidewalk is currently under renovation, based on city records indicating that the sidewalk is being repaired. Impact program 120 also determines that there is a flight of stairs five hundred feet and to the left of the user and a road to the right. Impact program 120 determines that the fact pattern matches several known patterns that are associated with injury of users. In this example and scenario, based, in part, on the mode of transportation of the user, each of the sidewalk, stairs, and the road may present a significant increase in risk of harm to the user if the user utilizes them. In some embodiments, impact program 120 predicts that there is a potentially hazardous situation/environment ahead of the user and warns the user of that potential hazard. In some embodiments, impact program 120 further provides one or both of (i) an alternate route based on a predicted or known destination of the user and (ii) a suggested change in activity, e.g., walking past the work zone instead of skateboarding. In some embodiments, similar to process 350, one or more caregivers are notified of the fact pattern and/or are informed of the fact pattern if the user fails to follow one or both of (i) the alternate route and/or (ii) the suggested change in activity. In such embodiments, the caregiver is typically presented with options during the setup of impact program 120 such that the caregiver is able to select various options to receive such notifications.

In decision process 340, impact program 120 determines whether the previously set threshold has been met or exceeded. In some embodiments and scenarios multiple factors are given weighted values when determining whether the threshold has been met or exceeded. For example, impact program 120 analyzes the data from portable computing devices 140 the user and determines that the pattern of impacts matches those of playing tennis. As such, impacts that involve the hand holding the racket are given a lower weight, i.e., the weight is decreased, when determining whether those impacts have exceeded the threshold. However, since the tennis court is a relatively hard surface and the severity of an injury may be increased, impacts that involve the user falling onto the tennis court are given a higher weight, i.e., the weight is increased, when determining whether those impacts have exceeded the threshold. As such, certain embodiments are able to modify the amount of measured impact that is required to meet or exceed the preset threshold by giving greater weight to certain types of impacts and/or less weight to other types of impacts depending on one or more of the activity being performed and one or more characteristics of the environment of the user. In another scenario and embodiment, the characteristics of the user are taken into account. For example, a user has a broken leg in a cast. Impact program 120, accounts for this fact pattern by increasing the weight applied to impacts that are determined to be the result of falling, i.e., if impact program 120 determines that the user has fallen down, a higher weight is applied to the impact since the restricted use of the broken leg may inhibit the ability of the user to minimize injury that can result from such a fall.

If impact program 120 determines that the threshold has not been met or exceeded (decision process 340, no branch), then impact program 120 returns to process 330 and continues to monitor and analyze the data. If impact program 120 determines that the threshold has been met or exceeded (decision process 340, yes branch), then impact program 120 proceeds to process 350. In some embodiments and scenarios, the threshold is determined to be met or exceeded based on a determination that a measured impact has exceeded the threshold for such impacts. In another embodiment and scenario, impact program 120 determines that a fact pattern in combination with an impact pattern dictate that the threshold has been met. For example, in continuation with the previous example of the skateboarding user, the user is sent the warning regarding the construction/repair of the sidewalk and impact program 120 determines that the user has failed to cease skateboarding but has still taken the stairs. Impact program 120 determines that the combination of environment (stairs) and the activity (skateboarding) represent an unacceptable increase risk of harm to the user and that the threshold has been exceeded, i.e., the weight applied to the impact data is increased such that the threshold is exceeded automatically.

In another example, impact program 120 determines that a user is swimming in a pool and has impacted their head against the side of the pool. In other situations, such a level of determined impact would present a relatively low risk of injury to the user. However, the activity of swimming elevates the risk associated with that impact to an unacceptable level of risk/potential harm to the user and impact program 120 determines that the threshold has been exceeded, i.e., impact program 120 increases the weight applied to the impact data such that the threshold is exceeded automatically.

In process 350, impact program 120 issues one or more alert messages. In some embodiments and scenarios, such alerts are sent to one or more of: the user, caregivers, first responders, police, or other designated personnel. The alert messages may include a query to the user, a last known location of the user, and a type of potential injury. The sending of such alerts may be sent immediately, based on magnitude of a given event (i.e., based on a determined severity of an impact), and/or sent as part of a daily report. Certain embodiments provide a cumulative analysis of impacts for a given user. In some embodiments, tracking of repetitive impact events injuries are leveraged to determine the potential for cumulative effects that result in injury. As such, while the threshold for impacts may not be exceeded, the cumulative effects of multiple low impacts can be predicted, and the user provided warning of such cumulative effects.

In some embodiments, a priority for contacts may be set such that alerts are sent to the next contact if the previous contact fails to respond in a timely fashion. For example, impact program 120 first sends a message to a user to inquire as to their status. After a threshold time period has passed without a response from the user, impact program 120 sends an alert to the first contact on the list of contacts. Such a contact pathway can be set in impact program 120 by the monitored person or a designated caregiver.

In some embodiments, layered on top of the risk implied by the force data is other risk data collected from other users, i.e., crowd-sourced data. This crowd-sourced data may be tied to a certain geolocation. As such, the crowd-sourced data can be interpreted as crowd-sourced force vector data that is aggregated to that geolocation. If a monitored person visits a location with historically high associated force risk, then that becomes part of the risk information for the monitored person and that user may be notified of the potential risk. For example, a user visits a particular abandoned building to which access is prohibited. As such, impact program 120 issues one or more alert messages to the user and the caregiver of that user.

Certain embodiments of the system leverage an artificial, i.e., computer based, neural network (NN). Such a neural network may be leveraged feature vectors to detect objects and/or structures in images captured by smart-devices. For example, a user is wearing a smart device that captures video data. Impact program 120 leverages the video data to perform object recognition and determines that there is a flight of stairs in front of the user. In another example, the smart device accesses a video camera attaches to the front of a bicycle and determines that there is an open sewer cover in the pathway of the bicycle. Impact program 120 is thus able to determine the potential for accidents based, in part, on image analysis/recognition and sends the user warnings accordingly.

Certain embodiments of the system leverage the neural network to make determinations based, in part, on geolocation. For example, a user is wearing a smart device that captures location information, such as GPS signals. Impact program 120 leverages the location information to perform searches, by generating search queries, based on the location. The search results are then analyzed to determine potential hazards that the location may present to the user. For example, certain roads may have higher levels of traffic and crossing them may be more hazardous to the user. Other areas may have a history of accidents occurring at or near that location. Impact program 120 is thus able to determine the potential for accidents based, in part, on the location of the user and sends the user warnings accordingly.

Figure 4:
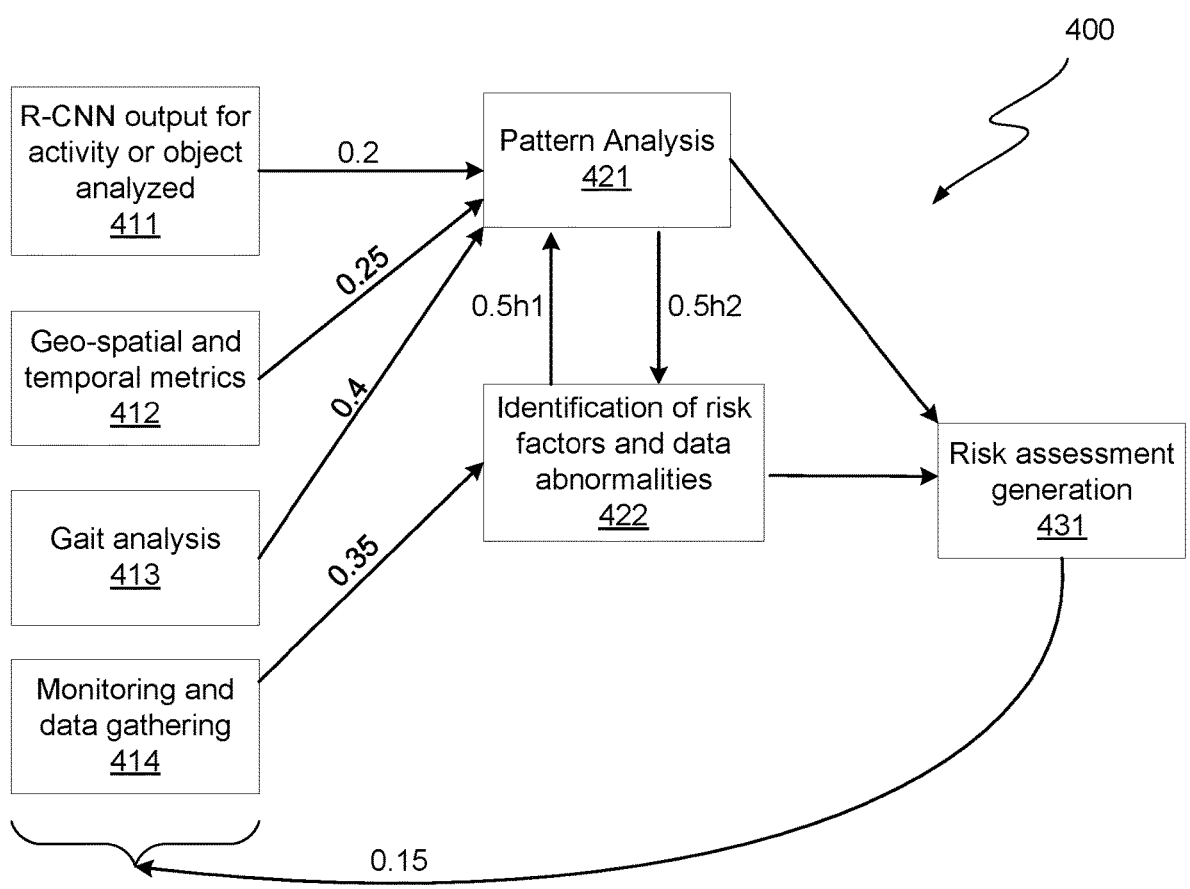
FIG. 4 illustrates a block diagram illustrating a weighting system that illustrates weights applied to various data types during and after an impact analysis, in accordance with an exemplary embodiment of the present invention.

FIG. 4 illustrates a block diagram illustrating a neural network, 400, that illustrates weights for the neural network being applied to various data types during and after an impact analysis, in accordance with an exemplary embodiment of the present invention.

In general, certain embodiments of impact program 120 leverage a neural network to perform certain operation based, in part, on accelerometer data and input to a deep learning neural network. Once this neural network model is trained, the neural network is used by impact program 120 to predict risk of trauma to the monitored person. As such, the following is to be understood as a description of various aspects and functionality of one or more embodiments of impact program 120.

In general, the weighting scheme is not accessible to the neural network user. The diagram depicted in FIG. 4 is an example of how a neural network itself works. The depicted neural network takes the training data and adjusts the weighting based on a process called back propagation. In this embodiment, to develop a model, training data is input into the neural network and the model "fit" algorithm adjusts the weights until a threshold of accuracy is reached for predicting risk.

Using a neural network may be seen as an enhanced embodiment to the operations as described with reference to other embodiments described herein. In some embodiments, a contextual analysis is generated by leveraging IP cameras in the vicinity of a given user, which are communicating with the user's mobile/wearable smart-devices, which may in-turn send data to other computing devices via network 130. For example, an aspect of impact program 120 is deployed that includes an image/visual analytics module running in a processor associated with one or more cameras monitoring user's activity, such as video device 230 and a camera included in smartphone 210. These image/visual analytics modules are running recognition and context neural network (R-CNN) object/activity analysis using a variety of machine learning algorithms. Over temporal period of training, this neural network system adapts to understanding the situations/context of the user, based in part on object recognition, in order to correlate the health metrics (being obtained by wearable/mobile devices) with said activities/ contextual situations. For example, for three sequential Thursdays at 4 PM, impact program 120 recognizes a tennis racket in image data and that the image of the tennis racket is followed by data that (i) indicates an increase in heart rate and blood pressure of the user, and (ii) is accompanied by a series of impacts for the users left arm. Based on the analysis of the fact pattern, impact program 120 "learns" that the user is likely left handed and plays tennis on Thursdays at 4 PM. Impact program 120 correlates changes to user biometric with these activities, which have been assessed via the neural network module, via continuous adjustment of weights associated with risk parameters using backpropagation. Once the correlations of these activities have been completed, anomalies/aberrations in one or more specific user's health metrics are determined and recorded by impact program 120 such that an action can be performed in response to (i) a threshold being met or exceeded and/or (ii) a prediction that a predicted cumulative effect meet a criteria that dictates the action be taken.

In situational analysis 411, a contextual analysis is performed that leverages image data processing, if image data is available, along with data associated with known activities and patterns associated with object impacts. The result of situational analysis 411 is an R-CNN output for activity and/or object detection.

In geo-spatial and temporal metrics 412, data such as latitude, longitude, and time of day are gathered based, at least in part, on a GPS location of at least one portable computing devices 140. Such data may be correlated and/or combined with internet available data, accessed via an automated search, to determine location-based metrics that are associated with a given fact pattern.

In gait analysis 413, a set of parameters are generated using historical gait data against which the characteristics of a current or recent gait of a user, associated with portable computing devices 140, can be compared. The parameters of a gait can include, but are not limited to, velocity and acceleration parameters.

In monitoring and data gathering 414 movement data, included as part of data 125, is gathered using sensors 145. In general, such data is gathered using at least sensors 145 but may further include sensors of other devices that are able to sense the movement or environment of a given user. The movement data included as part of data 125 may include, but is not limited to, accelerometer and magnetic sensor readings. In some embodiments and scenarios, a matrix is formed using the movement data.

In pattern analysis 421, as is illustrated in FIG. 4, pattern analysis 421 consumes data generated by situational analysis 411, geo-spatial and temporal metrics 412, gait analysis 413, and identification of risk factors and data abnormalities 422. Weights are applied to these respective sources of data as part of the neural network. Data from situational analysis 411 has an associated weighting of 0.2. Data from geo-spatial and temporal metrics 412 has an associated weighting of 0.25. Data from gait analysis 413 has an associated weighting of 0.4. Data from monitoring and data gathering 414 has an associated weight of 0.35. Data from pattern analysis 421 has an associated weighting of 0.5 h2. Data from identification of risk factors and data abnormalities 422 has an associated weighting of 0.5 h1. Finally, data from risk assessment generation 431 has an associated weighting of 0.15.

In general, the output of pattern analysis 421 indicates an impact pattern for an activity that is likely being performed by the user and may further include one or more environmental characteristics that are predicted to influence risks associated with that activity.

In identification of risk factors and data abnormalities 422, impact program 120 leverages the neural network to analyze the fact pattern, activity being performed by the user, and environmental characteristics to determine thresholds for risk factors and data abnormalities. Data generated by identification of risk factors and data abnormalities 422 is based, at least in part, on monitoring and data gathering 414 and the output of pattern analysis 421. For example, certain activities are known to have certain types of impacts associated with them. As such, impact program 120 sets the thresholds for such impacts based on the determination that the user is engaged in that particular activity. Impact program 120 may also take into account one or more characteristics of the user when determining what to set a threshold at for a given risk factor. For example, a user has a history for a type of heart condition. As such, impact program 120 sets the thresholds for heart rate and blood pressure thresholds based on both the type of activity and the type of heart condition. In another example, impact program 120 has determined that the user is riding a bicycle without wearing a helmet, in pattern analysis 421. As such, in identification of risk factors and data abnormalities 422, impact program 120 determines that there is an increased risk of head trauma in the event of an accident wherein the user is dismounted and impacts the ground and the threshold for impact is lowered accordingly.

As illustrated in FIG. 4, results generated by risk factors and data abnormalities 422 are feed back into pattern analysis 421 using an associated weighting of 0.5 h2. In this way, impact program 120 learns to better analyze and identify patterns of movement. For example, impact program 120 identifies impacts associated with the hand of the user as the user strikes a tennis ball while playing tennis. Impact program 120 also initially mis-identifies a user accidentally striking the pole of the tennis net with their hand as an "acceptable impact" since the initial assessment for the activity of tennis allows for similar impacts involving the hand. However, subsequent analysis in risk factors and data abnormalities 422 indicates that the impact is unacceptable based on the user suddenly ceasing game play and dropping the tennis racket, i.e., risk factors and data abnormalities 422 determines that such an impact exceeds the threshold. As such, this data is fed back into pattern analysis 421 to modify the threshold for impacts and pattern analysis. In this example, the pattern analysis is further modified to include a kinetic impact aspect based on an average weight of tennis balls and a determined range of speeds that the user can swing the racket at. Based on this modification, a re-analysis of the data in risk factors and data abnormalities 422 properly identifies the impact as an anomaly, i.e., a data abnormality that exceeds the threshold.

The results that are generated by pattern analysis 421 and identification of risk factors and data abnormalities 422 are fed into risk assessment generation 431. In risk assessment generation 431 a generation of a risk assessment is made based on the available data. For example, impact program 120 determines that there is a risk that the user may have broken a bone in their hand when it impacted the pole of the tennis net based on the initial velocity and deceleration of the hand. In this example, impact program 120 determines the potential for injury based, in part, on known average limits of the human body. In some embodiments, the weighted output of risk assessment generation 431 is leveraged by impact program 120 to modify the weight factors being applied to by situational analysis 411, geo-spatial and temporal metrics 412, gait analysis 413, and monitoring and data gathering 414. In other words, in this example, the results of risk assessment generation 431 have an associated weight of 0.15 and this weight is used to adjust the weights, i.e., to re-weight, data being generated by situational analysis 411, geo-spatial and temporal metrics 412, gait analysis 413, and monitoring and data gathering 414.

One having ordinary skill in the art will recognize that many modifications to such a neural network can be made without deviating from the spirit of this invention. As such, the example listed herein is to be interpreted as exemplary and not as limiting in scope.

Figure 5:
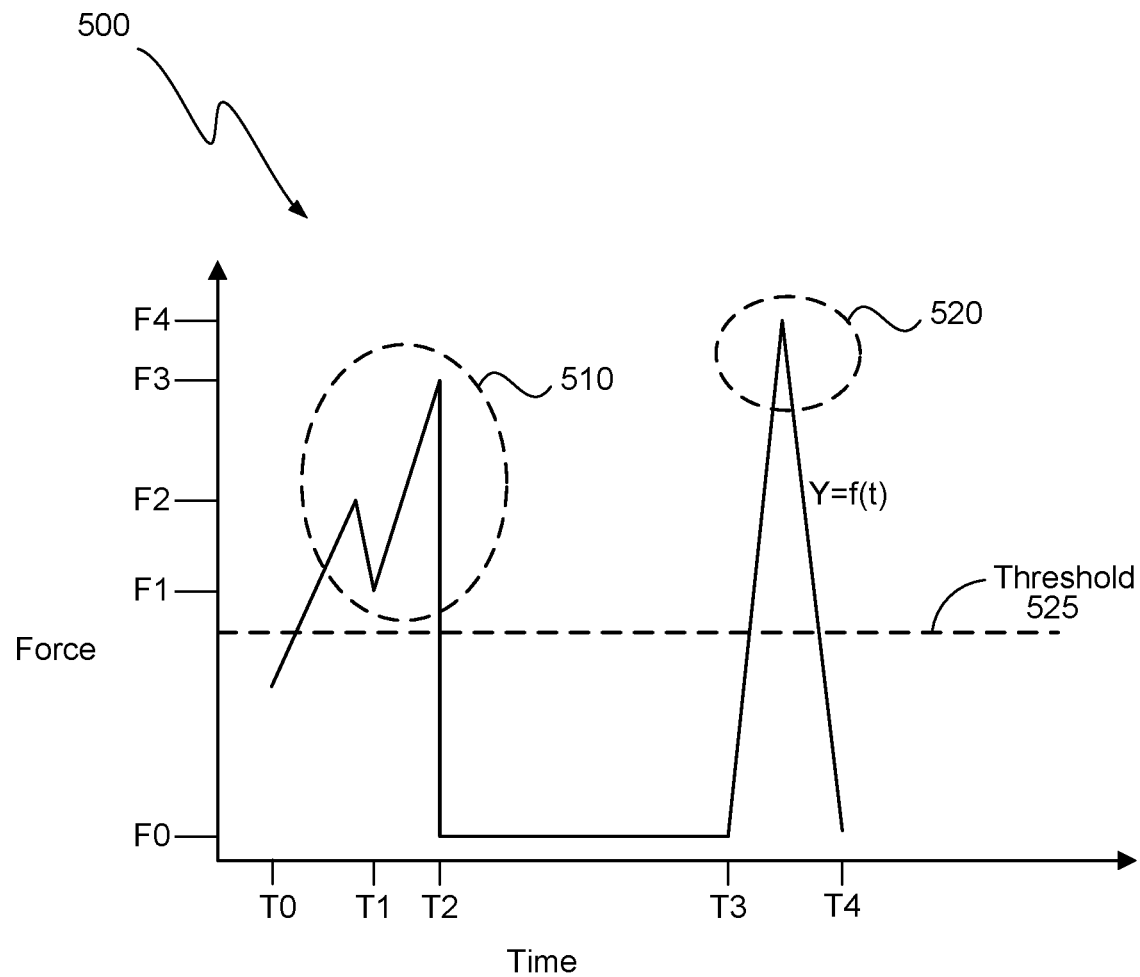
FIG. 5 illustrates an example of a graph analysis of force over time for an object, in accordance with an exemplary embodiment of the present invention.

FIG. 5 illustrates an example of a graph analysis, 500, of force over time for an object, in accordance with an exemplary embodiment of the present invention. In this example and embodiment, graph analysis 500 represents an output of risk factors and data abnormalities 422, which is leveraged by risk assessment generation 431 to generate a risk assessment.

For ease of understanding the physics being depicted in the graph, the graph can be interpreted as a toy car rolling down a hilly road. The accelerates downhill until car reaches the top of one hill when force is at F2 before beginning the climb of the next hill. At time T1, the car crests the second hill and begins its decent, accelerating until it reaches the halfway to the bottom of that hill at T2 where the toy car impacts a shrub and stops moving. The toy car is stationary between times T2 and T3. However, at T3 the toy car becomes unstuck and begins to accelerate down the hill again reaching force F4 between T3 and T4 where the toy car begins to get stuck in mud on the road, slowing, until it comes to a stop at T4. Note that no limitation is implied by the use of this example. As such, the example listed herein is to be interpreted as exemplary and not as limiting in scope.

In graph analysis 500, a line, Y=f(t), shows two events, 510 and 520, that exceed threshold 530. Event 510 includes two peaks, however, the dip separating them does not go below threshold 530. In contrast event 520 includes only a single peak. The peaks on this chart are the magnitude of the vectors that are occurring in a time series. The steepness of the vector is meaningful because this represents the acceleration data at a particular point in time.

In some embodiments, impact program 120 applies a classical physics (i.e., Newtonian physics) analysis to determine what is happening to the object. As such, a change in force over time is interpreted as an acceleration, which is seen as changes in the slope of the line where a "flat" horizontal portion of line indicates no acceleration during that time period. In this example, between T0 and T1 the increasing slope, up and to the right indicates an acceleration to a maximum force of F2 before decelerating to F1. Between T1 and T2 the increasing slope, up and to the right indicates an acceleration to a maximum force of F3 before decelerating to F0. Note that the vertical slope of the line indicates that the object suddenly came to an immediate stop. In this example, the from F3 to F0 represents an acceleration that goes from 10 to 0 meters per sec*2 in a fraction of a second, which is a relatively small amount of time. Such sudden changes in acceleration may be indicative of an impact, wherein the greater the change in acceleration, the greater the impact force is understood to be. In this example, impact program 120 determines that based on the time between T0 and T2 that the two peaks corresponding to F2 and F3 represent two identifying characteristics of an event, denoted herein as event 510. of note is that both of these impacts corresponding to F2 and F3 exceed threshold 525. In this analysis, while there was a deceleration from F2 to F1, F1 still exceeded threshold 525. As such, in this embodiment, both of these impacts, corresponding to F2 and F3, are considered aspects of the same event 510.

For clarity, imagine an object falling onto a trampoline versus the object falling onto a concrete sidewalk. The trampoline would slow the velocity of the object over a much greater period of time, e.g., half a second, and the impact would be greatly reduced. In contrast, the object falling onto the concrete sidewalk would experience an abrupt stop in which there would be a large deceleration for the object and the velocity of the object goes to zero almost instantaneously. Embodiments recognize that such abrupt changes in velocity, if they exceed a threshold, are understood to pose risks to users. As such, embodiments of the present invention provide analysis and identification of such events.

Continuing with the analysis of FIG. 5, there is a period between T2 and T3 where acceleration and velocity of the object are zero. In this example, this period represents the time following an impact where the object has ceased movement. In this example, impact program 120 further determines that based on the time between T3 and T4 that the single peak corresponding to F4 represents an identifying characteristic of an event, denoted herein as event 520. Also of note is that impact event 520 corresponding to F4 also exceeds threshold 525. As such, in this embodiment, both of these impacts, corresponding to events 510 and 520, are considered events that dictate a response from impact program 120, e.g., a message is sent to a user that experienced such events.

Some embodiments of the present invention encompass a system and method that can report the possibility and/or risk of a head injury to an individual carrying computing devices that include the programming to carry out the functions and features as described herein. An individual equipped as such does not require that individual to self-report incident of impact above a threshold of severity and can track such events over a length of time that might indicate an increased risk of a repetitive trauma type injury. In some embodiments of the present invention, a system learns patterns associated with certain behaviors, including patterns of impact that are associated with those behaviors, and can identify abnormalities in those patterns that indicate possible injury to the individual. Such abnormalities can then be leveraged to predict future shock events and pro-active responses can be suggested or initiated automatically.

Embodiments recognize that certain existing solutions for concussion detection require specialized equipment, such as instrumented helmets, embedded sensors in mouth guards, and contact sheets that can determine in real time, the force of impact at the sensor locale. Embodiments recognize that data generated by such specialized equipment can be accumulated and analyzed and determine the impact forces and trauma absorbed by an individual over time. Embodiments recognize that such specialized equipment is typically not worn by the majority of individuals and is often restricted to individuals involved in high risk endeavors. Therefore, such solutions are not applicable when addressing the thousands of people who receive traumatic brain injury (TBI) through falls and other accidents that occur as a result of daily life events. Daily life events include low risk activities that are not predicted to have a high chance of resulting in an injury to the person, in contrast to high risk activities such as, but not limited to, contact sports or other activities that routinely expose participants to impacts that can result in trauma injury.

The most common source of TBIs is fall injuries, which have been estimated to be responsible for 40% of all brain injuries in an average year. In general, it has been noted that falling is one of the leading causes of all TBI, followed by being struck by a blunt object and car accidents. Embodiments recognize that the majority of individuals involved in such events were not wearing, nor is it reasonable for them to wear, the specialized equipment that certain existing solutions for concussion detection require.

Further, embodiments recognize that many head injuries, that result from accidents associated with daily activities, may not show external damage and therefor may go unreported. Additionally, certain head injuries that stop short of being severe may become significant if there is a pattern of head trauma over a small number of days. In 2013, it has been estimated that about 2.8 million TBI-related emergency department (ED) visits occurred in the United States. Further, of those incidents, TBI was a diagnosis in more than 282,000 of those ED visits and included TBI alone or TBI in combination with other injuries. Embodiments further recognize that TBI contributed to the loss of 50,000 individuals associated with those ED visits.

Embodiments recognize that throughout a typical day, the cerebrospinal fluid surrounding the human brain serves to cushion delicate brain matter against low-level bumps and jostles. Embodiments recognize that concussions are the result of a sharp blow, movement, or jolt to the head. When the acceleration or deceleration of the head is above a threshold, the brain will impact against the inner side of the skull, causing a temporary loss of function and damage to the brain. While some such accelerations or decelerations of the head are easy to identify based on accounts of an incident and/or symptoms shown by the individual involved, others are less obvious.

Embodiments recognize that there is a growing prevalence of smart devices being routinely carried by individuals of all ages and professions throughout the day. Further, embodiments recognize that data is playing an increasing a key role in personal health. Embodiments recognize that typical smart devices and their data can be leveraged to correlate health risks and events with people in general. Embodiments recognize that by leveraging the increasingly prevalent smart devices an increasing number of individuals may be protected, at least in part, from some types of consequences of TBI. Embodiments recognize that individuals that use such smart devices may participate in the risk assessment area for with aggregated data and analytics. Embodiments recognize that hospitals, large public venue operators, and stadium owners and health practitioners, among others, can benefit from the analysis of such data. For example, the analysis of such data can indicate that certain areas in a facility/venue are associated with a disproportionate number of falling incidents and steps can be taken to reduce such incidents.

Embodiments recognize that smart wearable devices, such as user linked devices and nearby IP cameras in a given vicinity, can communicate with each other to detect or monitor the actions/activity of the respective user. Embodiments recognize that even when these devices are not linked, the device data can still be correlated based on time of an event such that the data from each device can be correlated after it is analyzed.

Some embodiments provide an initial training assessment. In one such initial training assessment, the normal walking vectors of a given user are trained using multi-variate geo-spatial and temporal metric dimensions. Some embodiments provide a multi-variate geo-spatial and temporal metric dimensions that takes into account variables such as, but not limited to, gait, normal velocity, and accelerated velocity for various activities, such as, for example, walking and running.

Some embodiments provide a collision vector detection. In one such collision vector detection, an embodiment leverages a Deep learning Neural Network (DLNN) model for risk factor evaluation and weights readjustment for the user. In one such embodiment, a DLNN machine learning algorithm takes into account input features pertaining to geo-spatial conditions and performs object detection gathered from a collision vector matrix. In one such embodiment, the collision vector matrix data comprises one or more of: (i) directional sensing (magnetic sensor reading) data gathered from a smart phone in conjunction with one or more linked wearable devices and/or (ii) data generated by linked wearable devices and learned turbulence and/or shock levels that are determined over a period of time. In one embodiment, the matrix further comprises of accelerometer reading, and abnormality activity detection. An abnormal detection may be, but is not limited to, a decrease in movement/velocity, a change in gait, a change in acceleration, or combination thereof. In general, such changes occur over a period of time that is associated with an increased likelihood of accident occurrence and/or injury to the individual, which may vary/be configured based on characteristics of the given individual.

In one embodiment, DLNN modelling is applied for assessing risk of accident occurrence and/or injury based in part on data of individuals that have one or more characteristics that are similar to that of the user. In some scenarios and embodiments, the use of such data is leveraged if there are concerns relating to the sharing of health data, and/or if there is lack of health and risk related data pertaining to a particular user. For example, an embodiment leverages feature matching for a user with "x" height, "y" weight, and "z" gait parameter with data of users with similar height, weight, and gait, and/or combinations thereof, to assess risks in response to a determination that an accident/impact has occurred.

In one embodiment, risk vectors are computed based on input collision vectors as described above. In one such embodiment, over a configurable time-period, risk abnormality is detected if the system detects an anomaly from a certain specific threshold in the collision vector readings obtained various monitoring devices or aggregated device data. In one such embodiment, a correlation engine, which consists of DLNN machine learning mechanism, is used for object detection and activity recognition of the user in order to determine or predict the level of impact by understanding the level of threshold from previous statistical health-risk data. In one such embodiment, the gait type, velocity and accelerometer data, device(s) orientation and rate of change during time-period are included as features used to detect and predict impact/injury risk.

In one embodiment, K-means clustering can be used to cluster similar impacts and activities in order to fortify the correlation of the collision vectors and the impact on the user once an anomalous event has been assessed. K-means clustering is a method of vector quantization that ca be used for cluster analysis in data mining. K-means clustering aims to partition a number (n) of observations into a number of clusters (K) in which each observation belongs to the cluster with the nearest mean, serving as a prototype of the cluster. This results in a partitioning of the data space into Voronoi cells, i.e., a partitioning of a plane into regions based on distance to points in a specific subset of the plane. That set of points (called seeds, sites, or generators) is specified beforehand, and for each seed there is a corresponding region consisting of all points closer to that seed than to any other.

In one embodiment, a similar type of K-means clustering is used to detect anomalies in normal movement and actions of the users, to detect a shift in the combination of key features that are above a threshold. In one such embodiment, an accumulated impact is determined based, in part, on an integral of an output classifier function, which can either act as a sudden step function, ramp function, or take sigmoid form. In one such embodiment, a binary classifier, in its simplest form, is used to classify the abnormality as low, medium, or high risk of accident/injury of the user.

In one embodiment, a system can anonymously report increased events an or increased risk areas to a crowd-sourced user-risk database. In one such embodiment, when a user falls, even if an impact is not recognized as having a potential high risk for concussion/injury, the event can be further followed up by a brief questionnaire being sent to the user. For example, the questionnaire prompts the user to indicate whether any head impact was made with a hard surface, or whether there was a pronounced jerking of the head without impact. In one such embodiment, the system alerts or reports possible concussion events/or an increased risk thereof to guardians, primary physicians, and/or another type of assigned individual associated with the user.

In at least one embodiment, digital messages are sent based on impacts that are detected or predicted for a user. Impact program 120 receives data from at least one computing device affixed to a user, wherein the data corresponds to a pattern of movement of the user. Impact program 120 determines that the user is performing an activity that has an associated known pattern of impacts. Impact program 120 generates a customized pattern of impacts for the activity by modifying the known pattern of impacts based, at least in part, on the pattern of movement of the user. Impact program 120 generates a message based, at least in part, on a comparison of measured movement data of the user and the customized pattern of impacts.

In at least one embodiment, impact program 120 modifies the message to include an indication of a determination that one or more measured impacts deviate from the customized pattern of impacts.

In at least one embodiment, impact program 120 determining that one or more measured impacts deviate from the customized pattern of impacts by at least a threshold amount. Impact program 120 sending a query to the user, wherein the query is generated based, at least in part, on a determination that the one or more measured impacts correlate to a potential for injury of the user.

In at least one embodiment, impact program 120 modifies the message to include an indication of a predicted risk of injury based, at least in part on a predicted cumulative effect of impacts on the user over time.

In at least one embodiment, impact program 120 modifies a recipient list of the message to include a given recipient based, at least in part, on a setting and passage of a period of time. Impact program 120 sending the message to at least the given recipient.

In at least one embodiment, impact program 120 identifies the activity that the user is performing based, at least in part, on a comparison of the pattern of movement of the user with a plurality of known patterns of impacts that are respectively associated with different activities. Impact program 120 determining that the user is performing the activity based on a best fit analysis of the pattern of movement of the user and the associated known pattern of impacts.

In at least one embodiment, impact program 120 determines that the user is performing the activity based, at least in part, on a history of the user performing a type of activity at a given time, wherein the data was captured during the given time.

Figure 6:
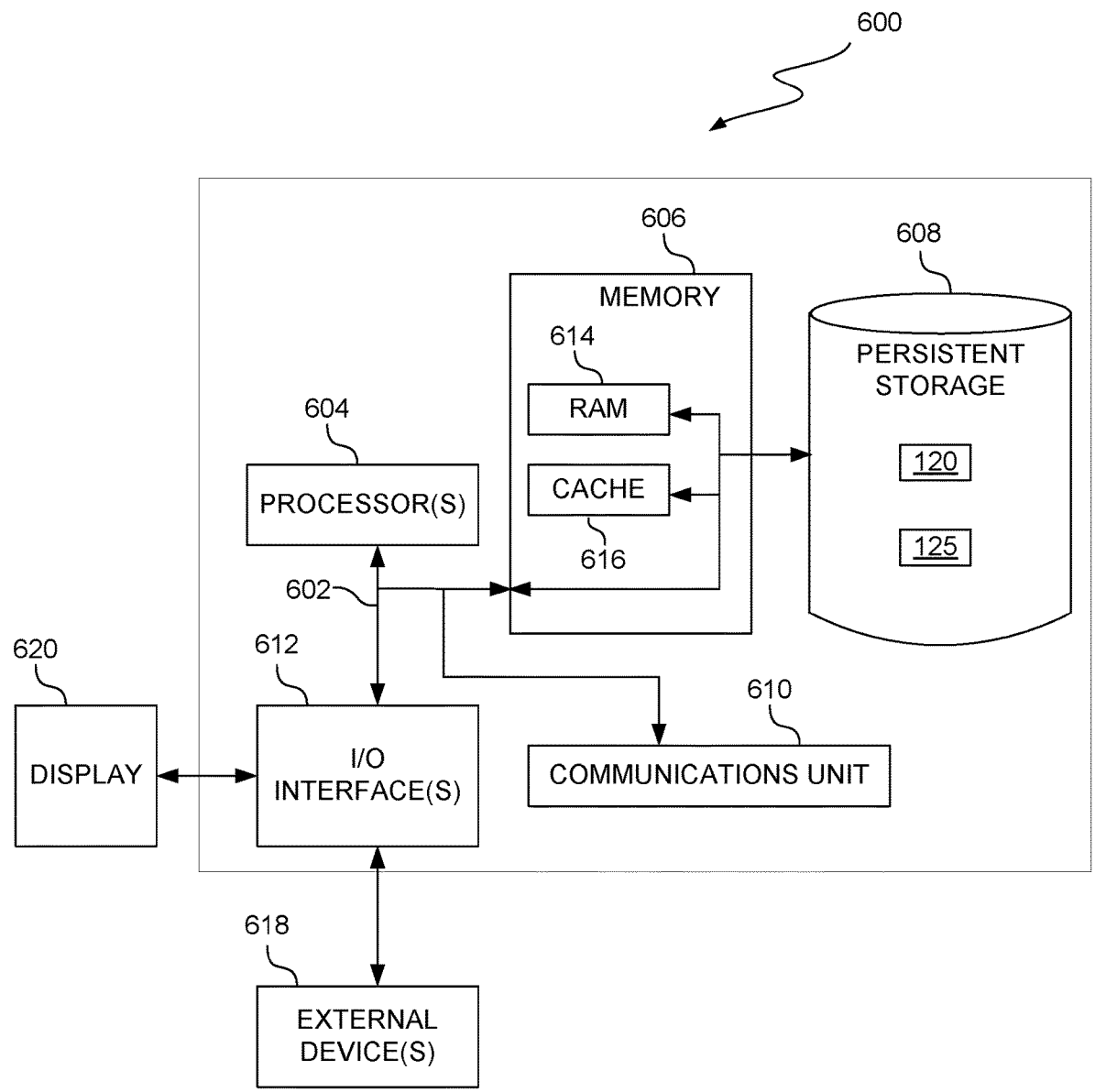
FIG. 6 depicts a block diagram of components of computing device that is the executing impact program of FIG. 1, and further illustrates certain components included in portable computing devices of FIG. 1, in accordance with an exemplary embodiment of the present invention.

FIG. 6 depicts a block diagram, 600, of components of computing device 105 that is executing impact program 120, and illustrates certain components included in portable computing devices 140, in accordance with an exemplary embodiment of the present invention. It should be appreciated that FIG. 6 provides only an illustration of one implementation and does not imply any limitations with regard to the environments in which different embodiments may be implemented. Many modifications to the depicted environment may be made.

Computing device 105 and portable computing devices 140 may respectively include communications fabric 602, which provides communications between computer processor(s) 604, memory 606, persistent storage 608, communications unit 610, and input/output (I/O) interface(s) 612. Communications fabric 602 can be implemented with any architecture designed for passing data and/or control information between processors (such as microprocessors, communications and network processors, etc.), system memory, peripheral devices, and any other hardware components within a system. For example, communications fabric 602 can be implemented with one or more buses.

Memory 606 and persistent storage 608 are computer-readable storage media. In this embodiment, memory 606 includes random access memory (RAM) 614 and cache memory 616. In general, memory 606 can include any suitable volatile or non-volatile computer-readable storage media.

Impact program 120 and data 125 are stored in persistent storage 608 for execution and/or access by one or more of the respective computer processors 604 via one or more memories of memory 606. In this embodiment, persistent storage 608 includes a magnetic hard disk drive. Alternatively, or in addition to a magnetic hard disk drive, persistent storage 608 can include a solid state hard drive, a semiconductor storage device, read-only memory (ROM), erasable programmable read-only memory (EPROM), flash memory, or any other computer-readable storage media that is capable of storing program instructions or digital information.

The media used by persistent storage 608 may also be removable. For example, a removable hard drive may be used for persistent storage 608. Other examples include optical and magnetic disks, thumb drives, and smart cards that are inserted into a drive for transfer onto another computer-readable storage medium that is also part of persistent storage 608.

Communications unit 610, in these examples, provides for communications with other data processing systems or devices, including resources of network 130. In these examples, communications unit 610 includes one or more network interface cards. Communications unit 610 may provide communications through the use of either or both physical and wireless communications links. Impact program 120 and data 125 may be downloaded to persistent storage 608 through communications unit 610.

I/O interface(s) 612 allows for input and output of data with other devices that may be connected to network 130. For example, I/O interface 612 may provide a connection to external devices 618 such as a keyboard, keypad, a touch screen, and/or some other suitable input device. External devices 618 can also include portable computer-readable storage media such as, for example, thumb drives, portable optical or magnetic disks, and memory cards. Software and data used to practice embodiments of the present invention, e.g., Impact program 120 and data 125, can be stored on such portable computer-readable storage media and can be loaded onto persistent storage 608 via I/O interface(s) 612. I/O interface(s) 612 also connect to a display 620.

Display 620 provides a mechanism to display data to a user and may be, for example, a computer monitor, or a television screen.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

It is to be noted that the term(s) such as, for example, "SMALLTALK" and the like may be subject to trademark rights in various jurisdictions throughout the world and are used here only in reference to the products or services properly denominated by the marks to the extent that such trademark rights may exist.

It is apparent that there has been provided approaches for event identification and/or notification of an event occurring. While the invention has been particularly shown and described in conjunction with exemplary embodiments, it will be appreciated that variations and modifications will occur to those skilled in the art. Therefore, it is to be understood that the appended claims are intended to cover all such modifications and changes that fall within the true spirit of the invention.

What is claimed is:

1. A computer-implemented method, the method comprising: receiving, by one or more computer processors, data corresponding to a plurality of movement patterns of a user, wherein the data is received from (i) at least one video recording device within a defined area, and (ii) crowd-sourced data including force vector data that is aggregated from a plurality of individuals across one or more geolocations;
  determining, by one or more computer processors, the plurality of movement patterns relates to a previously engaged activity, wherein the previously engaged activity matches a known pattern of impacts within a given threshold;
  generating, by the one or more computer processors, a customized pattern of impacts for the user by modifying the known pattern of impacts based, at least in part, on the plurality of movement patterns of the user; and
  generating, by the one or more computer processors, a response alert, wherein the response alert includes the customized pattern of impacts for the user.

2. The computer-implemented method of claim 1, the method further comprising:
  modifying, by the one or more computer processors, the response alert to include an indication of a determination that one or more measured impacts deviate from the customized pattern of impacts.

3. The computer-implemented method of claim 1, the method further comprising:
  determining, by the one or more computer processors, that one or more measured impacts deviate from the customized pattern of impacts by at least a threshold amount; and
  sending, by the one or more computer processors, a query to the user, wherein the query is generated based, at least in part, on a determination that the one or more measured impacts correlate to a potential for injury of the user.

4. The computer-implemented method of claim 1, the method further comprising:
  modifying, by the one or more computer processors, the response alert to include an indication of a predicted risk of injury based, at least in part on a predicted cumulative effect of impacts on the user over time.

5. The computer-implemented method of claim 1, the method further comprising:
modifying, by the one or more computer processors, a recipient list of the response alert to include a given recipient based, at least in part, on a setting and passage of a period of time; and
sending, by the one or more computer processors, the response alert to at least the given recipient.

6. The computer-implemented method of claim 1, the method further comprising:
identifying, by the one or more computer processors, the previously engaged activity based, at least in part, on a comparison of the plurality of movement patterns of the user with the known pattern of impacts within the given threshold.

7. The computer-implemented method of claim 1, the method further comprising:
determining, by the one or more computer processors, the plurality of movement patterns based, at least in part, on a history of the user performing a type of activity at a given time, wherein the data was captured during the given time.

8. A computer program product, the computer program product comprising a computer readable storage medium having program instructions stored thereon, wherein the computer readable storage medium is not a transitory signal per se, the stored program instructions comprising:
program instructions to receive data corresponding to a plurality of movement patterns of a user, wherein the data is received from (i) at least one video recording device within a defined area, and (ii) crowd-sourced data including force vector data that is aggregated from a plurality of individuals across one or more geolocations;
program instructions to determine the plurality of movement patterns relates to a previously engaged activity, wherein the previously engaged activity matches a known pattern of impacts within a given threshold;
program instructions to generate a customized pattern of impacts for the user by modifying the known pattern of impacts based, at least in part, on the pattern of plurality movement patterns of the user; and
program instructions to generate a response alert, wherein the response alert includes the customized pattern of impacts for the user.

9. The computer program product of claim 8, the method stored program instructions further comprising:
program instructions to modify the response alert to include an indication of a determination that one or more measured impacts deviate from the customized pattern of impacts.

10. The computer program product of claim 8, the stored program instructions further comprising:
program instructions to determine that one or more measured impacts deviate from the customized pattern of impacts by at least a threshold amount; and
program instructions to send a query to the user, wherein the query is generated based, at least in part, on a determination that the one or more measured impacts correlate to a potential for injury of the user.

11. The computer program product of claim 8, the stored program instructions further comprising:
program instructions to modify the response alert to include an indication of a predicted risk of injury based, at least in part on a predicted cumulative effect of impacts on the user over time.

12. The computer program product of claim 8, the stored program instructions further comprising:
program instructions to modify a recipient list of the response alert to include a given recipient based, at least in part, on a setting and passage of a period of time; and
program instructions to send the response alert to at least the given recipient.

13. The computer program product of claim 8, the stored program instructions further comprising:
program instructions to identify the previously engaged activity based, at least in part, on a comparison of the plurality of movement patterns of the user with the known pattern of impacts within the given threshold.

14. The computer program product of claim 8, the stored program instructions further comprising:
program instructions to determine the plurality of movement patterns based, at least in part, on a history of the user performing a type of activity at a given time, wherein the data was captured during the given time.

15. A computer system, the computer system comprising:
one or more computer processors;
at least one computer readable storage medium that is not a transitory signal per se; and
program instructions stored on the at least one computer readable storage medium, the stored program instructions being executable by at least one computer processor of the one or more computer processors, the stored program instructions comprising:
program instructions to receive data corresponding to a plurality of movement patterns of a user, wherein the data is received from (i) at least one video recording device within a defined area, and (ii) crowd-sourced data including force vector data that is aggregated from a plurality of individuals across one or more geolocations;
program instructions to determine the plurality of movement patterns relates to a previously engaged activity, wherein the previously engaged activity matches a known pattern of impacts within a given threshold;
program instructions to generate a customized pattern of impacts for the user by modifying the known pattern of impacts based, at least in part, on the pattern of plurality movement patterns of the user; and
program instructions to generate a response alert, wherein the response alert includes the customized pattern of impacts for the user.

16. The computer system of claim 15, the stored program instructions further comprising:
program instructions to modify the response alert to include an indication of a determination that one or more measured impacts deviate from the customized pattern of impacts.

17. The computer system of claim 15, the stored program instructions further comprising:
program instructions to determine that one or more measured impacts deviate from the customized pattern of impacts by at least a threshold amount; and
program instructions to send a query to the user, wherein the query is generated based, at least in part, on a determination that the one or more measured impacts correlate to a potential for injury of the user.

18. The computer system of claim 15, the stored program instructions further comprising:

program instructions to modify the response alert to include an indication of a predicted risk of injury based, at least in part on a predicted cumulative effect of impacts on the user over time.

19. The computer system of claim 15, the stored program instructions further comprising:

program instructions to modify a recipient list of the response alert to include a given recipient based, at least in part, on a setting and passage of a period of time; and program instructions to send the response alert to at least the given recipient.

20. The computer system of claim 15, the stored program instructions further comprising:

program instructions to identify the previously engaged activity the user is performing based, at least in part, on a comparison of the plurality of movement patterns of the user with the known pattern of impacts within the given threshold.

* * * * *